United States Patent
Bjurbo et al.

(10) Patent No.: US 12,220,544 B2
(45) Date of Patent: Feb. 11, 2025

(54) AIRWAY DETECTION USING ULTRASOUND

(71) Applicant: Avent, Inc., Alpharetta, GA (US)

(72) Inventors: Karl Thomas Bjurbo, Cumming, GA (US); James F. Tassitano, Marietta, GA (US); David M. Page, Cumming, GA (US); Hilton M. Kaplan, New York, NY (US); Don J. McMichael, Roswell, GA (US)

(73) Assignee: Avent, Inc., Alpharetta, GA (US)

( * ) Notice: Subject to any disclaimer, the term of this patent is extended or adjusted under 35 U.S.C. 154(b) by 0 days.

(21) Appl. No.: 16/944,696

(22) Filed: Jul. 31, 2020

(65) Prior Publication Data
US 2022/0032010 A1    Feb. 3, 2022

(51) Int. Cl.
*A61M 25/01* (2006.01)
*A61B 8/00* (2006.01)
*A61B 8/12* (2006.01)

(52) U.S. Cl.
CPC .......... *A61M 25/0158* (2013.01); *A61B 8/12* (2013.01); *A61B 8/42* (2013.01); *A61B 8/445* (2013.01);
(Continued)

(58) Field of Classification Search
CPC ...... A61M 25/0158; A61M 2205/3375; A61M 2210/1025; A61M 2210/1042; A61B 8/12; A61B 8/42; A61B 8/445; A61B 8/56
See application file for complete search history.

(56) References Cited

U.S. PATENT DOCUMENTS

| | | |
|---|---|---|
| 5,785,051 A | 7/1998 | Lipscher et al. |
| 6,349,720 B1 | 2/2002 | Clark |

(Continued)

FOREIGN PATENT DOCUMENTS

| | | |
|---|---|---|
| EP | 0 626 818 B1 | 5/2002 |
| WO | WO 93/14689 A2 | 8/1993 |

(Continued)

OTHER PUBLICATIONS

Pankaj Kundra et al., "Ultrasound of the airway," 2011, Indian Journal of Anaesthesia, vol. 55, Issue 5, pp. 456-462 (Year: 2011).*

(Continued)

*Primary Examiner* — Joseph M Santos Rodriguez
*Assistant Examiner* — Maria Christina Talty
(74) *Attorney, Agent, or Firm* — Meunier Carlin & Curfman LLC

(57) ABSTRACT

A tubing assembly for use with electronic catheter guidance systems is provided and includes a catheter, an ultrasound transducer disposed within the catheter, and an optional additional external ultrasound transducer. The catheter extends in a longitudinal direction and has a proximal end and a distal end defining a lumen therebetween. Further, the catheter is configured for placement within a patient's digestive tract or respiratory tract. The ultrasound transducer can be located within the catheter's lumen, and the optional external ultrasound transducer can be located on or outside the patient's body. Both ultrasound transducers can transmit ultrasound signals as directed by a processor and can communicate with the processor to deliver ultrasound data to a display device. The attenuation of the ultrasound energy at a selected frequency can indicate placement of the catheter in the digestive tract or respiratory tract. A catheter guidance system and method of use are also provided.

7 Claims, 9 Drawing Sheets

(52) U.S. Cl.
CPC ....... *A61B 8/56* (2013.01); *A61M 2205/3375* (2013.01); *A61M 2210/1025* (2013.01); *A61M 2210/1042* (2013.01)

(56) References Cited

U.S. PATENT DOCUMENTS

| | | | |
|---|---|---|---|
| 6,705,319 B1 | 3/2004 | Wodicka et al. | |
| 6,913,259 B2 | 7/2005 | Phinney et al. | |
| 6,918,391 B1 | 7/2005 | Moore | |
| 7,603,159 B2 | 10/2009 | Rasche | |
| 7,996,059 B2 | 8/2011 | Porath et al. | |
| 8,038,629 B2 | 10/2011 | Solanki et al. | |
| 8,147,413 B2 | 4/2012 | Abraham | |
| 8,394,031 B2 | 3/2013 | Mansy et al. | |
| 8,617,152 B2 | 12/2013 | Werneth et al. | |
| 8,834,370 B2 | 9/2014 | Evert et al. | |
| 8,923,949 B2 | 12/2014 | Amit et al. | |
| 9,004,069 B2 | 4/2015 | Efrati et al. | |
| 9,031,638 B2 | 5/2015 | Su | |
| 9,486,595 B2 | 11/2016 | Borrye et al. | |
| 9,700,693 B2 | 7/2017 | Qiu | |
| 9,707,363 B2 | 7/2017 | Mansfield et al. | |
| 9,861,776 B2 | 1/2018 | Lin et al. | |
| 10,206,607 B2 | 2/2019 | Prough et al. | |
| 10,219,777 B2 | 3/2019 | Freeman et al. | |
| 10,226,608 B2 | 3/2019 | Imran | |
| 10,383,646 B2 | 8/2019 | Baker et al. | |
| 10,478,072 B2 | 11/2019 | Tearney et al. | |
| 10,512,452 B2 * | 12/2019 | Labyed | G16H 50/30 |
| 10,595,773 B2 | 3/2020 | Calabró et al. | |
| 2003/0034035 A1 | 2/2003 | Raphael | |
| 2006/0081255 A1 * | 4/2006 | Miller | A61B 8/0833 128/207.14 |
| 2008/0146940 A1 * | 6/2008 | Jenkins | G01S 15/899 600/463 |
| 2008/0183080 A1 | 7/2008 | Abraham | |
| 2013/0158537 A1 | 6/2013 | Deladi et al. | |
| 2016/0022943 A1 | 1/2016 | Kanowitz | |
| 2016/0279366 A1 | 9/2016 | Mansfield et al. | |
| 2017/0128039 A1 | 5/2017 | Waldstreicher et al. | |
| 2017/0143258 A1 | 5/2017 | Calabró et al. | |
| 2017/0340522 A1 * | 11/2017 | Mansfield | A61B 7/008 |
| 2018/0168540 A1 | 6/2018 | Van Bruggen et al. | |
| 2019/0029642 A1 * | 1/2019 | De Cicco | A61B 8/06 |
| 2019/0030312 A1 | 1/2019 | Davis et al. | |
| 2019/0038862 A1 | 2/2019 | Mansfield | |
| 2019/0069876 A1 * | 3/2019 | Michaeli | A61B 8/4477 |
| 2019/0261958 A1 * | 8/2019 | Groenland | A61B 8/445 |
| 2019/0340837 A1 * | 11/2019 | Shmayahu | A61B 18/1492 |
| 2020/0129145 A1 | 4/2020 | Abbasi | |
| 2020/0214663 A1 * | 7/2020 | Shin | A61B 8/12 |

FOREIGN PATENT DOCUMENTS

| | | |
|---|---|---|
| WO | WO 2016/200334 A1 | 12/2016 |
| WO | WO 2019/186589 A1 | 10/2019 |
| WO | WO 2020/044758 A1 | 3/2020 |

OTHER PUBLICATIONS

Vijaya Chockalingam et al., "Thyroid and Parathyroid Ultrasound and Ultrasound-Guided FNA," Chapter 4, 2018, Springer, pp. 71-94 (Year: 2018).*

International Search Report and Written Opinion for PCT/US2020/042996, dated Nov. 2, 2021, 15 pages.

* cited by examiner

AIRWAY DETECTION USING ULTRASOUND

FIELD OF THE INVENTION

The subject matter of the present invention relates generally to a system and method for detection placement of a medical device in the airway using ultrasound technology.

BACKGROUND

Physicians and other health care providers frequently use catheters to treat patients. The known catheters include a tube which is inserted into the human body. Certain catheters are inserted through the patient's nose or mouth for treating the gastrointestinal tract. These catheters, sometimes known as enteral catheters, typically include feeding tubes. The feeding tube lies in the stomach or intestines, and a feeding bag delivers liquid nutrient, liquid medicine or a combination of the two to the patient.

When using these known enteral catheters, it is important to place the end of the catheter at the proper location within the human body. Erroneous placement of the catheter tip may injure or harm the patient. For example, if the health care provider erroneously places an enteral catheter into the patient's trachea, lungs, or other regions of the respiratory system rather than through the esophagus and to the stomach to reach the desired location in the digestive tract for delivering nutrients or medicine, liquid may be introduced into the lungs with harmful, and even fatal, consequences. Further, there is a risk of a puncturing the lungs during placement, which could result in a pneumothorax. In particular, the esophagus of the digestive tract and the trachea of the respiratory system are in close proximity to each other and are blind to the health care provider during catheter placement, which creates a dangerous risk for erroneous catheter placement.

In some cases, health care providers use X-ray machines to gather information about the location of catheters within the body. There are several disadvantages with using X-ray machines. For example, these machines are relatively large and heavy, consume a relatively large amount of energy and expose the patient to a relatively high degree of X-ray radiation. Also, these machines are typically not readily accessible for use because, due to their size, they are usually installed in a special X-ray room. This room can be far away from the patient's room. Therefore, health care providers can find it inconvenient to use these machines for performing catheter insertion procedures. Moreover, even X-rays are not necessarily conclusive as to the location of the catheter tip, as the natural and continuous movement of the internal organs can make it difficult for the physician interpreting the X-ray to be sure of the actual location of the distal end of the catheter. In addition, using X-ray technology is expensive and is a time-consuming task that can create unnecessary delays in delivering critical nutrients to the patient.

Another existing catheter locating means involves using an electromagnetic coil positioned inside the catheter and an electromagnetic coil locating receiver outside of the patient's body. The electromagnetic coil is generally incorporated into a stylet or guide wire which is inserted within the catheter. The coil locating receiver can be used to determine the distance the coil is from the receiver and its depth in the patient's body and can communicate with a display to show a reference image of a non-subject body and an image of the coil located on the display with the reference image. The coil locating receiver is a large device that must rest in a precise location outside the patient's body and does not permit for adjustments due to each individual patient's anatomical size or shape. However, a patient undergoing a feeding tube placement will be agitated and sudden movements are expected, which can move the coil locating receiver, thus increasing the likelihood of positional errors or complications in locating the catheter. Additionally, these existing systems can only display the coil location over a reference image of a non-subject (i.e., a generic patient) body without reference to the individual patient's particular anatomy. Thus, these existing systems can only generate generic warnings or alerts when a deviation from an intended path within the body is estimated.

Consequently, there is a need for a system for notifying a user of the positioning of a medical device within a patient's body in real-time to ensure more accurate catheter placement. In particular, a notification system that is easy to use, provides a clear deviation alert when the medical device is improperly positioned and can be used in conjunction with electromagnetic location tracking to confirm medical device placement would also be useful.

SUMMARY

Objects and advantages of the invention will be set forth in part in the following description, or may be obvious from the description, or may be learned through practice of the invention.

In one particular embodiment of the present invention, a tubing assembly is provided. The tubing assembly includes a catheter and an ultrasound transducer. The catheter has a proximal end and a distal end and extending in a longitudinal direction, wherein the proximal end and the distal end define a lumen therebetween. Further, the catheter is configured for placement within a digestive tract of a patient.

In one embodiment, the ultrasound transducer can be located within the lumen of the catheter.

In another embodiment, the ultrasound transducer can be located at the distal end of the catheter.

In yet another embodiment, the ultrasound transducer can be configured to transmit ultrasound energy as controlled by a processor in real-time. Further, the ultrasound transducer can be configured for a wired connection or a wireless connection to the processor. In addition, the ultrasound transducer can be further configured to receive ultrasound energy and send signals related to the received ultrasound energy to the processor.

In still another embodiment, the ultrasound transducer can include a piezoelectric component.

In another embodiment of the present invention, a catheter guidance system is provided. The catheter guidance system includes: (a) a processor; (b) a power source; and (c) a tubing assembly. Further, the tubing assembly includes a catheter having a proximal end and a distal end and extending in a longitudinal direction, wherein the proximal end and the distal end define a lumen therebetween; and an ultrasound transducer. The ultrasound transducer transmits and/or receives ultrasound energy as controlled by the processor in real-time via an electrical connection. In addition, ultrasound data from the ultrasound transducer is communicated to the processor in real-time via an electrical connection, and the catheter guidance system alerts a user as to placement of the catheter in a digestive tract of a patient or alerts the user as to placement of the catheter in a respiratory tract of the patient.

In one embodiment, the catheter guidance system can further include a memory device storing instructions which, when executed by the processor, cause the processor to (i)

interpret the ultrasound data communicated to the processor and (ii) cause the catheter guidance system to alert the user as to placement of the catheter in the digestive tract of the patient or alert the user as to placement of the catheter in the respiratory tract of the patient based on the interpretation of the ultrasound data.

Further, the processor can interpret the ultrasound data by determining a degree of attenuation of ultrasound signals, time-of-flight of ultrasound signals, or ultrasound imaging.

In addition, the degree of attenuation of ultrasound energy delivered at a frequency of about 20 kilohertz to about 2.5 megahertz can be used to determine if the placement of the catheter is in the digestive tract or the respiratory tract.

In another embodiment, the ultrasound transducer can be located within the lumen of the catheter at the distal end of the catheter.

In yet another embodiment, the ultrasound transducer can include a piezoelectric component.

In still another embodiment, the system can include an external ultrasound transducer configured to transmit ultrasound energy to the ultrasound transducer of the tubing assembly and/or receive ultrasound energy transmitted by the ultrasound transducer of the tubing assembly.

Further, the external ultrasound transducer can be configured to be placed on or near the patient's throat or chest.

In another particular embodiment of the present invention, a method for determining if a catheter is placed within a digestive tract of a body of a patient is provided. The method includes: (a) inserting a distal end of a tubing assembly into an orifice of the body, wherein the tubing assembly includes the catheter, wherein the catheter has a proximal end and a distal end and extends in a longitudinal direction, wherein the proximal end and the distal end define a lumen therebetween; and an ultrasound transducer; (b) electrically connecting the ultrasound transducer to a processor via a wired connection or a wireless connection; (c) activating the ultrasound transducer, wherein the ultrasound transducer transmits and/or receives ultrasound energy as controlled by the processor in real-time via an electrical connection; (d) advancing the distal end of the catheter inside the body in a direction away from the orifice while the ultrasound transducer is activated; (f) communicating ultrasound data from the ultrasound transducer to the processor in real-time via the wired connection or the wireless connection; and (g) informing a user as to placement of the catheter in the digestive tract of the patient or respiratory tract of the patient based on the ultrasound data received by the processor.

In one embodiment, a memory device can store instructions which, when executed by the processor, cause the processor to (i) interpret the ultrasound data communicated to the processor and (ii) cause a display device to communicate whether or not the catheter is placed within the digestive tract of the patient based on the interpretation of the ultrasound data.

In another embodiment, the processor can interpret the ultrasound data by determining a degree of attenuation of ultrasound signals, time-of-flight of ultrasound signals, or ultrasound imaging. Further, the degree of attenuation of ultrasound energy delivered at a frequency of about 20 kilohertz to about 2.5 megahertz can be used to determine if the placement of the catheter is in the digestive tract or the respiratory tract.

In still another embodiment, the method can further include the steps of placing an external ultrasound transducer on or near the patient's body, wherein the external ultrasound transducer is electrically connected to the processor via a wired connection or a wireless connection; and activating the external ultrasound transducer to transmit ultrasound energy and/or receive ultrasound energy transmitted by the ultrasound transducer of the tubing assembly.

Further, the frequency and intensity of the ultrasound energy transmitted by the ultrasound transducer of the tubing assembly and/or the external ultrasound transducer can be selected to be detectable by the other of the ultrasound transducer of the tubing assembly or the external ultrasound transducer when the ultrasound transducer of the tubing assembly is located in the digestive tract and not detectable by the other of the ultrasound transducer of the tubing assembly or the external ultrasound transducer when the ultrasound transducer of the tubing assembly is located in the respiratory tract.

In addition, the processor can be configured to measure attenuation of the transmitted ultrasound energy.

These and other features, aspects, and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended figures, in which.

DETAILED DESCRIPTION

Figure 1:
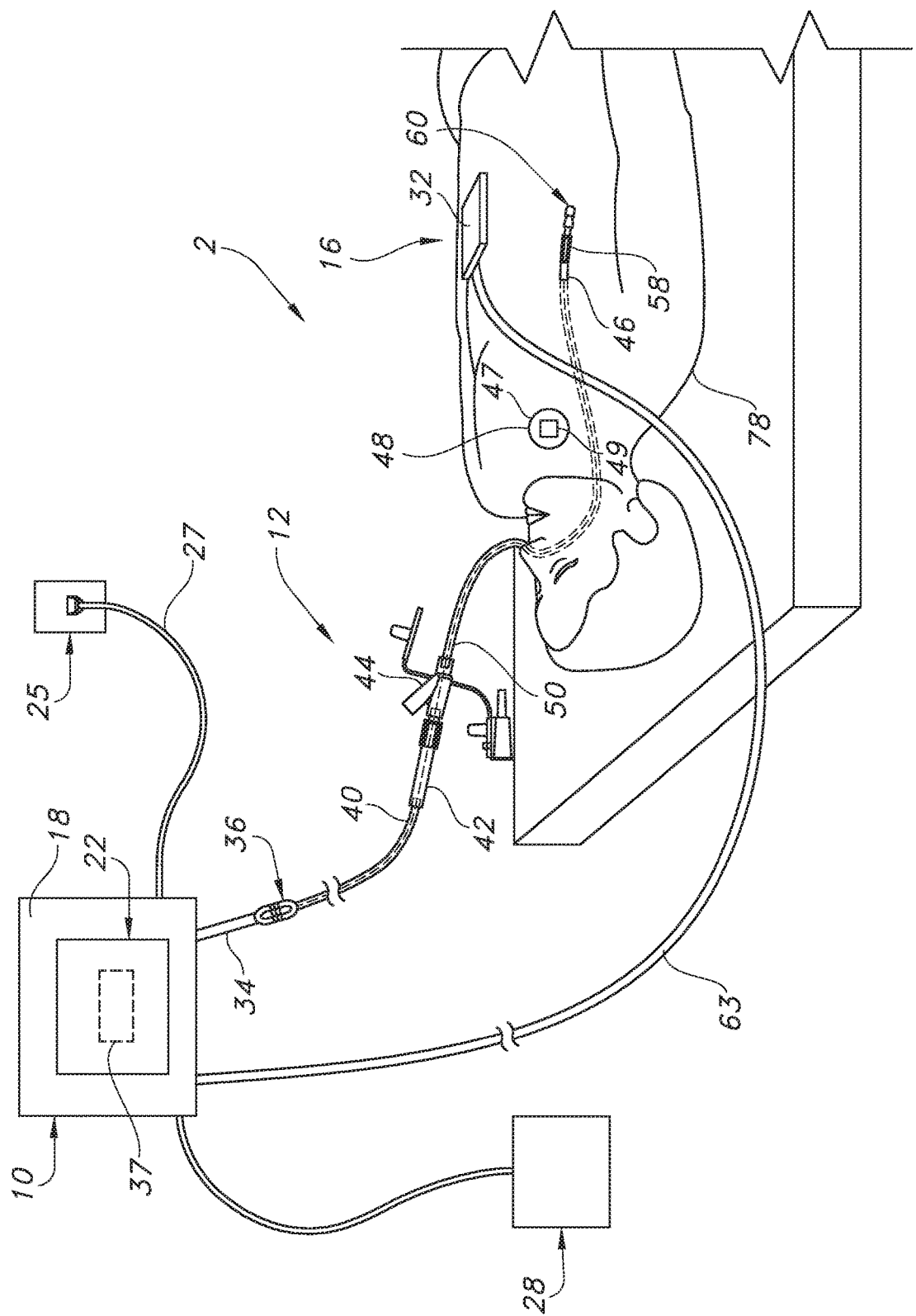
FIG. 1 is a perspective view of the catheter guidance system of the present invention illustrating the display device, electronic catheter unit, external ultrasound transducer and the ultrasound transducer that is at least temporarily contained with the electronic catheter unit as it is being used to position a catheter within a patient in one embodiment of the present invention.

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used with another embodiment to yield a still further embodiment. Thus, it is intended that the present invention covers such modifications and variations as come within the scope of the appended claims and their equivalents.

As used herein, the terms "about," "approximately," or "generally," when used to modify a value, indicates that the value can be raised or lowered by 5% and remain within the disclosed embodiment. Further, when a plurality of ranges are provided, any combination of a minimum value and a maximum value described in the plurality of ranges are contemplated by the present invention. For example, if ranges of "from about 20% to about 80%" and "from about 30% to about 70%" are described, a range of "from about 20% to about 70%" or a range of "from about 30% to about 80%" are also contemplated by the present invention.

Generally speaking, the present invention is directed to a tubing assembly that includes a catheter having a proximal end and a distal end and extending in a longitudinal direction, where the proximal end and the distal end define a lumen therebetween. Further, the catheter can be configured for placement within a digestive tract or a respiratory tract of a patient. The tubing assembly also includes an ultrasound transducer. The ultrasound transducer can be located within the lumen of the catheter. The ultrasound transducer can be used in conjunction with an external ultrasound transducer or receiver located on or outside the patient's body. The ultrasound transducer of the tubing assembly can transmit ultrasound signals as directed by a processor, and the external ultrasound transducer can receive ultrasound signals from the ultrasound transducer of the tubing assembly and communicate with a processor to deliver sound data to a display device. A catheter guidance system and a method for accurately placing a catheter in the digestive tract or respiratory tract are also contemplated by the present invention.

The present inventors have found that the tubing assembly, catheter guidance system, and method described in more detail herein allow for the ultrasound data captured in real-time via an ultrasound transducer or receiver positioned just outside the patient's body to be used to determine if the distal end of the catheter is placed within the digestive tract (e.g., the epiglottis, esophagus, stomach, intestines, etc.) rather than placed within the respiratory system (e.g., the trachea, bronchi, lungs, etc.), where such placement could be harmful and even fatal to a patient. Further, the present inventors have found that because the external ultrasound transducer or receiver can obtain measurements and communicate those measurements to processor and ultimately a display device or other communication device (e.g., a phone, pager, etc.) in real time, the placement of the catheter can be confirmed within seconds of a catheter placement procedure, which can save valuable time, resources, and cost while at the same time limit patient risk in the event of the erroneous placement of the catheter.

Specifically, the present inventors have found that capturing and monitoring ultrasound data in real-time transmitted from inside or within a catheter to be placed in a predetermined location along the digestive tract (e.g., esophagus, stomach, intestines, etc.), which is facilitated by the ultrasound transducer of the catheter guidance system of the present invention, allows for the efficient and accurate placement of the catheter within the digestive tract at a low cost. For instance, an ultrasound transducer or receiver placed outside the patient's body, e.g., on the throat or xyphoid process, can capture ultrasound data (e.g., ultrasound waves that propagate from the ultrasound transducer at a distal end of the catheter to the external ultrasound transducer or receiver) as the catheter is being directed by a health care provider in to the body of a patient, where the captured ultrasound data can then be transmitted to a display device via a processor. The health care provider can then view the captured ultrasound data on the display device (e.g., on a spectrogram that plots the captured ultrasound data of a graph showing frequency versus time to determine attenuation of the ultrasound signal) to determine if the catheter has been placed in the digestive tract or placed in an anatomical region of the respiratory system (e.g., the trachea, bronchi, lungs, etc.). Alternatively or additionally, a memory device that can include machine readable instructions and one or more computer programs (which, for example, may include a plurality of algorithms) can be used by the processor to process the data from the ultrasound transducer, where the display device can then indicate the catheter information to the health care provider in the form of a signal as to whether the catheter is placed in the digestive tract or placed within, for instance, a portion of the respiratory system. For example, a green check mark or the word "Yes" can be displayed on the screen to indicate accurate placement of the catheter within the digestive or gastrointestinal tract, while a red circle with a diagonal line through it, an "X", or the word "No" can be displayed on the screen for erroneous placement, such as placement within the respiratory system.

The various features of the catheter guidance system are discussed in detail below.

Referring now to the drawings, in an embodiment illustrated in FIGS. 1-4, the catheter guidance system 2 contemplated by the present invention includes: (a) an apparatus 10 having a housing 18 which supports a controller or processor 20 which may include filter 38 and a display device 22; (b) a power cord 27 that couples the apparatus 10 to a power source 25; (c) an optional printer 28 coupled to the apparatus 10 for printing out paper having graphics which indicate catheter location information; (d) an optional non-invasive movable receiver-transmitter or transceiver 32 electronically coupled to the processor 20 by a wire, cable, signal data connection or signal carrier 63; and (e) an invasive electronic catheter unit 12 in communication with and operatively coupled to the apparatus 10 where the electronic catheter unit 12 includes a tubing assembly 14 that includes a catheter 50; an ultrasound transducer 46; and an optional signal generator 58 when the system 2 includes the optional non-invasive movable receiver-transmitter or transceiver 32. An external ultrasound transducer or receiver 48 may additionally be included in the electronic catheter unit 12 or alternatively separate from but in operative communication with the electronic catheter unit 12. The invasive catheter unit 12 may be an electronic catheter unit that is be operatively coupled to the apparatus 10 by a wire, cable, cord or electrical extension 34, which, in turn, is operatively coupled to the processor 20.

Figure 2:
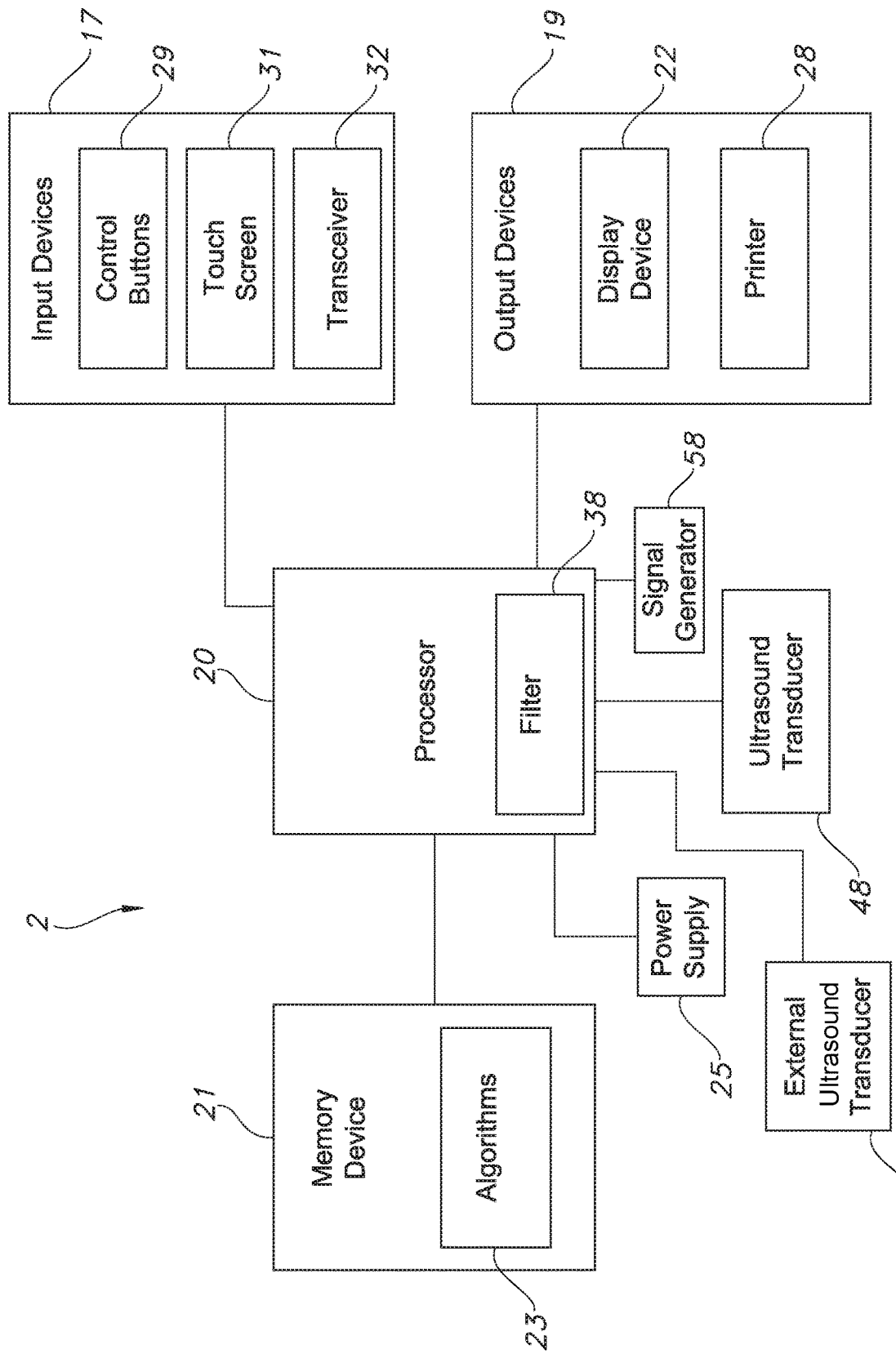
FIG. 2 is a schematic block diagram of the electronic configuration of the catheter position guidance system illustrating the processor, memory device, internal and external ultrasound transducers, input devices, output devices, and optional signal generating assembly according to one embodiment of the present invention.

As best illustrated in FIG. 2, the system 2, in one embodiment, includes: (a) a plurality of input devices 17 for providing input signals to the system 2 such as one or more control buttons 29, a touch screen 31, and the optional transceiver 32; (b) an ultrasound transducer 46 that can continuously transmit ultrasound waves from inside or within a catheter 50 of the tubing assembly 14 in real-time; (c) an external ultrasound transducer or receiver 48 that can continuously capture ultrasound data received from the transmitted ultrasound waves from the ultrasound transducer 46 in real-time; (d) an optional signal generator 58 which produces or generates electronic signals that are received by the transceiver 32; (e) a memory device 21 including machine readable instructions and one or more computer programs (which, for example, may include a plurality of algorithms 23) which are used by the processor 20 (which may include a filter 38) to instruct the ultrasound transducer 46 to transmit ultrasound waves and to process the ultrasound data captured by the external ultrasound transducer or receiver 48 as well as to process the signal data produced by the signal generator 58 and transmitted by the transceiver 32 if present; and (f) a plurality of output devices 19 such as the display device 22 and the printer 28 which indicate the catheter information to the health care provider, such as in the form of a graph 37 (see FIG. 1). The display device 22 may be any suitable display mechanism including, but not limited to, a liquid crystal display (LCD), light-emitting diode (LED) display, cathode-ray tube display (CRT) or plasma screen.

In one particular embodiment, the memory device 21 can store instructions which, when executed by the processor 20, cause the processor 20 to (i) interpret catheter 50 location and/or position information as determined and communicated by the ultrasound transducer 46 and/or the external ultrasound transducer or receiver 48 and the optional signal generating assembly 16 and the non-invasive transceiver 32, and (ii) cause the processor 20 to then instruct the system 2 to alert the health care provider either via the display device 22, auditory signals, etc. as to the accurate or inaccurate placement of the catheter 50.

Figure 3:
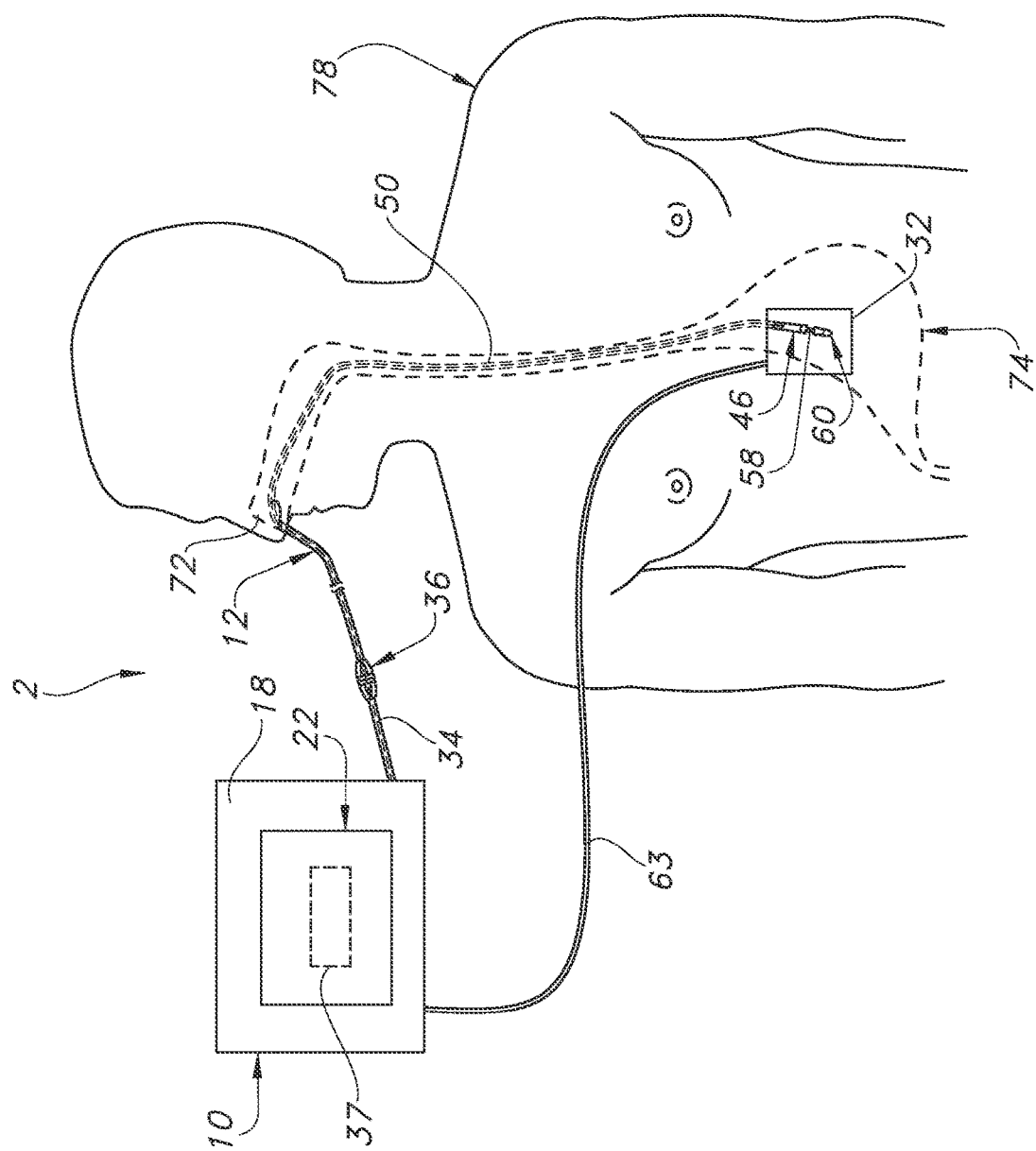
FIG. 3 is a top or plan view of the electronic catheter unit and the display device illustrating an enteral application involving a catheter inserted into a human body and indication of ultrasound information (e.g., a graph or image) on the display device.

Health care providers can use the system 2 in a variety of catheter applications. In one example illustrated in FIG. 3, the system 2 is used in an enteral application. Here, a portion of the electronic catheter unit 12 is placed through an orifice 72 of the patient's body 78, such as the patient's nose or mouth. The distal end or tip 60 of the electronic catheter unit 12 can ultimately by positioned in the stomach 74. As the health care provider advances the catheter 50 of the electronic catheter unit 12 towards the patient's stomach 74, the ultrasound transducer 46 can transmit ultrasound waves, e.g., from the distal end 60 of the catheter 50. The ultrasound transducer 46 can then receive reflected or echoed ultrasound waves, and/or the external ultrasound transducer or receiver 48 can continuously monitor for ultrasound waves that propagate from the ultrasound transducer 46 of the catheter 50 to the external ultrasound transducer or receiver 48 as the catheter 50 is inserted by the health care provider, whether the external ultrasound transducer or receiver 48 is placed on or near the patient's body 78, as shown in FIGS. 1 and 3. The display device 22 and the printer 28 can indicate information related to the location of the portion of the electronic catheter unit 12 within the body 78 based on the ultrasound data acquired by the ultrasound transducer 46 of the catheter 50 and/or the external ultrasound transducer or receiver 48, as well as information related to the shape of the pathway taken by the catheter unit 12 if the system includes the signal generator 58 and the associated non-invasive transceiver 32. It should be appreciated that the system 2 need not indicate the exact location or path of the catheter unit 12 to provide assistance to the health care provider.

Figure 4:
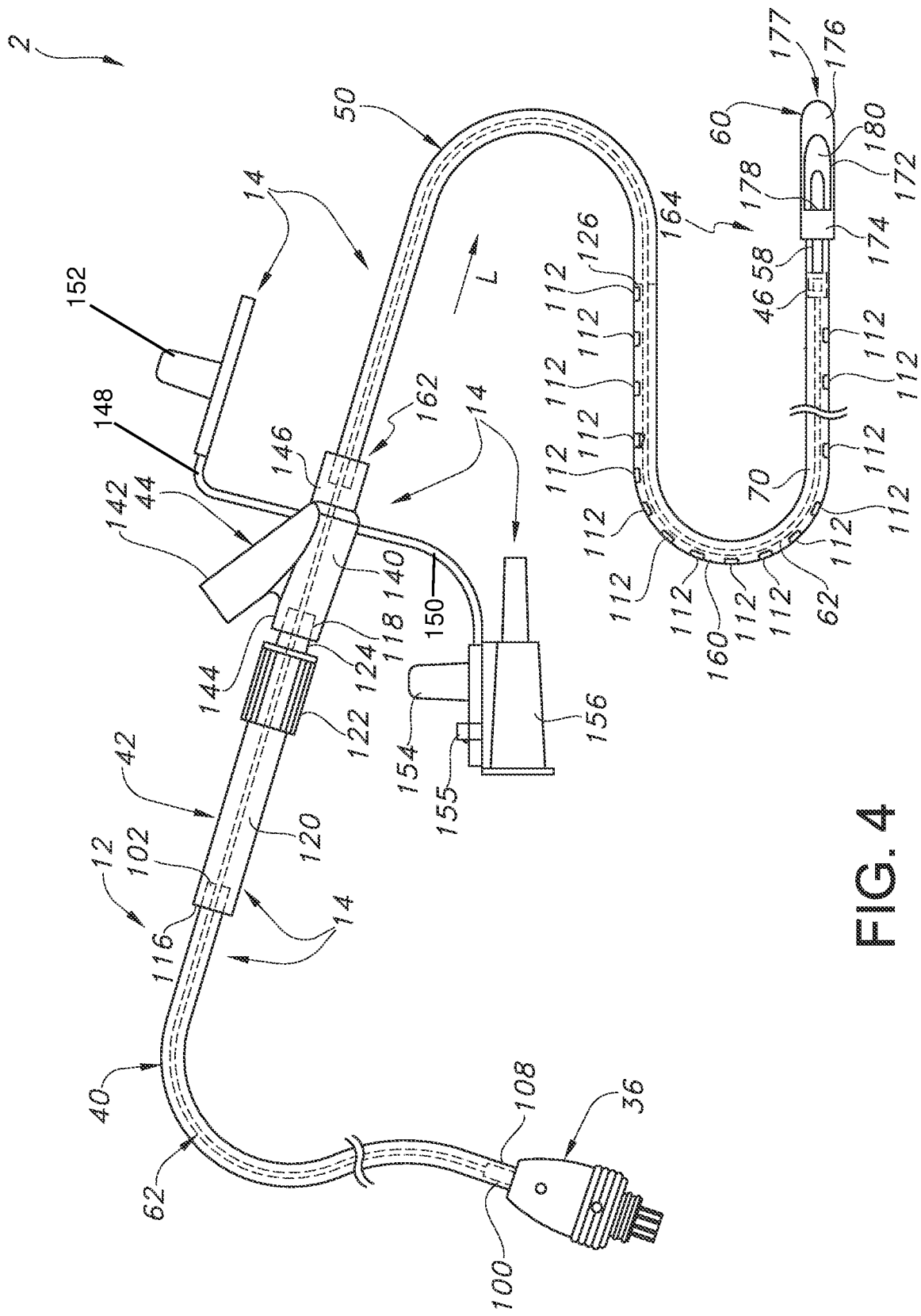
FIG. 4 is a perspective view of the electronic catheter unit illustrating the tubing assembly according to various embodiments of the present invention.

Referring to FIG. 4, in one embodiment, the electronic catheter unit 12 includes a tubing assembly 14, which includes the catheter 50 and the ultrasound transducer 46 of the present invention, where the catheter 50 can generally extend in the longitudinal direction L. In one embodiment, the ultrasound transducer 46 can be disposed within the lumen 70 of the catheter 50 at a distal end or tip 60 of the catheter 50, as shown in FIG. 4. However, it is also to be understood that the ultrasound transducer 46 can be located anywhere along the length of the catheter 50, so long as the sound waves generated by the transmitter 46 within the catheter 50 can reach or be picked up by the external ultrasound transducer 48, and the distance from the ultrasound transducer 46 to the distal end 60 of the catheter 50 is known.

Figure 5:
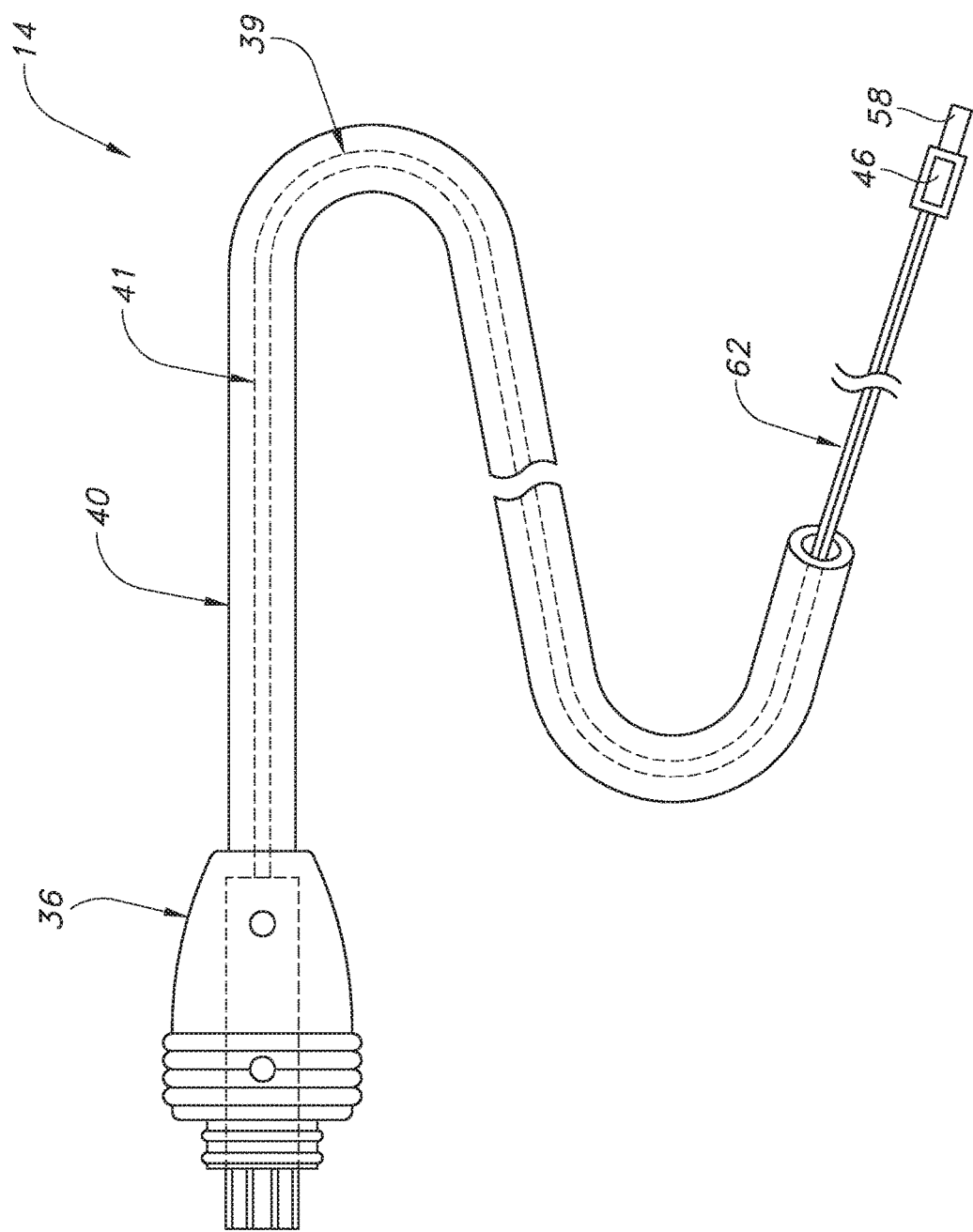
FIG. 5 is a perspective view of the ultrasound transducer portion of the electronic catheter unit according to one embodiment of the present invention.

As best illustrated in FIGS. 4-5, in one embodiment, such as when a wired connection (e.g., a connection via a wire assembly 62 as opposed to a wireless connection, which is also contemplated by the present invention, where the ultrasound transducer 46 includes a battery or other source of power) electrically connects the ultrasound transducer 46 to the processor 20, the tubing assembly 14 can include (a) a tube or an electrical tubular insulator 40; (b) a mid-connector or union device 42 which receives the tubular insulator 40; (c) a multi-port connector or y-port connector 44 attachable to the union device 42; (d) a catheter 50, such as a feeding tube, connected to the y-port connector 44; and (e) a distal end or tip 60 of the catheter 50, where the ultrasound transducer 46 can be located within the lumen 70 of the catheter 50 at the distal end or tip 60 or anywhere upstream along the length of the catheter 50.

In one embodiment, the tubular insulator 40 includes a tube having a proximal end 100 attachable to an attachment member or neck 108 of a controller coupler or electrical connector 36 and a distal end 102 receivable by the union device 42; and an internal diameter which is substantially equal to or greater than an external diameter of a wire assembly 62 described below, which can serve as the hard wired electrical connection between the ultrasound transducer 46 and the processor 20, so as to slide over the wire assembly 62. In another embodiment, the tubular insulator 40 may fit relatively tightly over the wire assembly 62 so as to be secured to the wire assembly 62.

As best illustrated in FIG. 4, in one embodiment, the union device 42 includes: (a) a proximal end 116; (b) a distal end 118; (c) a position adjuster, extender or elongated neck 120 positioned between the proximal end 116 and the distal end 118; (d) a grasp or gripping member 122 positioned adjacent to the distal end 118 so as to assist users in grasping and manipulating the union device 42; and (e) an insert 124 positioned adjacent to the gripping member 122 which is received by the y-port connector 44. When assembled, the proximal end 116 of the union device 42 is coupled to the distal end 102 of the tubular insulator 40.

In one embodiment, the multi-port or y-port connector 44 includes: (a) a body 140; (b) a liquid delivery branch, medicine delivery branch or medicine branch 142 attached to the body 140 for distributing drugs, medicine or other medicinal liquids to the patient's body 78; (c) a nutrient delivery branch or feeding branch 144 attached to the body 140 and sized to receive the insert 124 of the union device 42; (d) a catheter or feeding tube connection branch 146 attached to the catheter 50; (e) a flexible or movable arm 148 attached to the body 140; and (f) a flexible or movable arm 150 attached to the body 140. In an alternative embodiment, y-port connector 44 includes additional branches for administering various nutrients or medicines to the body 78. In another alternative embodiment, the y-port connector 44 includes only a feeding branch 144 and a connection branch 146. The arm 148 has a stopper 152, and the arm 150 has a stopper 154. The stoppers 152 and 154 are sized to prevent fluid from passing through the branches 142 and 144 after such branches 142 and 144 are plugged with stoppers 152 and 154, respectively. In addition, the arm 150 includes a fastener 155 which secures a tube-size adapter 156 to the arm 150. The tube-size adapter 156 enables fluid delivery tubes (not shown) having various diameters to connect to the feeding branch 144 of the y-port connector 44.

As illustrated in FIG. 4, in one embodiment, the catheter 50 includes a feeding tube or catheter 50 with a body 160 having a proximal end 162 attached to the catheter connection branch 146 of the y-port connector 44 and a distal end 164. The proximal end 162 is insertable into the catheter connection branch 146 of the y-port connector 44 so as to bring the catheter 50 into fluid communication with the y-port connector 44.

As also shown in FIG. 4, in one embodiment, the end member, bolus or tip 60 is attached to the distal end 164 of the catheter 50. The tip 60 includes a body 172 having a collar 174 and an end member 176. The body 172 defines a passage 178 and an opening 180. The opening 180 is positioned between the collar 174 and the end member 176. A portion 177 of the end member 176 can have a rounded shape. The shape of the passage 178 and opening 180 of the tip 60 is configured to facilitate the flow of fluid from the catheter 50 into the patient's body 78 while decreasing the likelihood that the opening 180 will become clogged.

The tubular connector 40, union device 42, y-port connector 44, catheter 50, and tip 60 can be made from any suitable polymer or plastic material including, but not limited to, polyamide, polyethylene, polypropylene, polyurethane, silicone and polyacrylonitrile.

Referring still to FIGS. 1 and 4, when the ultrasound transducer 46 is located in the lumen 70 of the catheter 50 such as at its distal end 60, the ultrasound transducer 46 can be electrically connected to the processor 20 via an electrical connection in the form of a wire assembly 62 that runs through the tubular insulator 40 described above to an electrical connector or controller coupler 36, discussed in more detail below. This arrangement can also be used when the electrical connection from the ultrasound transducer 46 to the processor 20 is wireless.

Turning now to the specifics of the ultrasound transducer 46 and referring to FIGS. 1, 4, and 5, a controller coupler or an electrical connector 36 can be operatively connected to the electrical extension 34 and an elongated wire assembly 62 can be operatively coupled to the electrical connector 36 to form a wired connection between the ultrasound transducer 46 and the processor 20, although it is to be understood that the electrical connection between the processor 20 and the ultrasound transducer 46 can also be wireless provided that the ultrasound transducer 46 has its own power source, such as a battery. Further, a wire or elongated stiffener 39 can be attached to the connector 36 and can serve as a support for the wire assembly 62 when it is inserted into the body 160 of the catheter 50 or the tubing 66. Further, the tubular insulator 40 described above can cover a portion 41 of the wire assembly 62 positioned adjacent to the connector 36 in the embodiment where the ultrasound transducer 46 is positioned within the lumen 70 of the catheter 50. In any event, the electrical connector or controller coupler 36 can provide the electrical connection between the apparatus 10 and the ultrasound transducer 46 when the ultrasound transducer 46 is hard wired to the catheter guidance system 2 via the wire assembly 62. In other embodiments, the ultrasound transducer 46 can be in the form of an echogenic material that is configured to transmit and/or reflect ultrasound waves. The echogenic material can be incorporated into the catheter 50, e.g., at the tip 60 of the catheter 50. For instance, the ultrasound transducer 46 can be a piezoelectric bimorph or unimorph configured to function as both a receiver and transmitter of ultrasound energy. The echogenic material or piezoelectric bimorph/unimorph may be mounted to the catheter 50 on the inside or outside of the catheter 50, or may be incorporated into the material of the catheter 50 itself.

Turning now to the specific configuration for the ultrasound transducer 46, although any suitable ultrasound transducer 46 for transmitting ultrasound waves that propagate from the distal end 60 of the catheter 50 that can withstand the environmental conditions of the body can be used in the catheter guidance system 2 of the present invention, in one particular embodiment, the ultrasound transducer 46 can be in the form of a transducer having a small footprint such that it can be placed within the lumen 70 of the catheter 50 or any other suitable location within the tubing assembly 14. The ultrasound transducer 46 may be any suitable transducer now known or later developed in the art. For example, in one embodiment, the ultrasound transducer 46 may be a piezoelectric (PZT) transducer. Alternatively, the transducer 46 may be a capacitive micromachined ultrasonic transducer (CMUT). In yet another embodiment, the transducer 46 may also include polydimethylsiloxane (PDMS) transducers and/or photoacoustic transducers.

As shown in FIGS. 1 and 3, the external ultrasound transducer 48 can be placed on or near the patient's body 78. For instance, the external ultrasound transducer 48 can include a housing 49 and an attachment 47. The attachment 47 can be directly affixed to the subject's body 10 so that the external ultrasound transducer 48 maintains a fixed reference point in relation to the patient's body 78. Thus, if the patient moves, the external ultrasound transducer 48 can move with the patient to maintain a static frame of reference with respect to the particular patient. The attachment 47 can be positioned on a surface of the housing 49. For example, the attachment 47 can include an adhesive material that is configured to affix the housing 49 to the skin of the subject, a patch on the subject's body, or a garment worn by the subject. The adhesive material can be an adhesive substrate that can be adhesive on both sides such that it adheres to the surface of the housing 49 on one side and to a subject's body or garment on the other side. When the attachment 47 is adhesive material adhered to the surface of the housing 49, it may additionally include a peelable protective sheet covering the entire adhesive material. The peelable protective sheet can be removed prior to affixing the adhesive attachment 47 to the patient's body 78 or the patient's garment. For instance, the attachment 47 can be similar to an EKG pad in which the attachment 47 includes an adhesive sheet surrounding the housing 49 such as in a donut shape. In other embodiments, the attachment 47 can include a clip, pin, magnet, hook and loop system, or any other suitable means for affixing the housing 49 of the external ultrasound transducer 48 to the patient's body 78 or garment. Further, the attachment 47 can be or can include ultrasound gel to provide a means for transmission of the ultrasonic energy between the body and the external ultrasound transducer 48. The gel could be in the form of a hydrogel adhesive, or it could be applied/dispersed from a bottle during placement of the external ultrasound transducer 48.

In any event, by using an attachment 47 on the external ultrasound transducer 48 that can affix the external ultrasound transducer 48 to the patient's body 78 or garment, the frame of reference of the measurement of the sound waves from the ultrasound transducer 46 can remain stationary with the patient's body. Alternatively, the external ultrasound transducer 48 can be placed near the patient's body 78, such as at the patient's bedside. In some embodiments, the external ultrasound transducer 48 may be incorporated into the housing 18 of the system 2.

Turning now to the specific configuration for the external ultrasound transducer 48, although any suitable ultrasound transducer 48 for transmitting and/or receiving data from ultrasound waves that propagate from the ultrasound transducer 46 in the distal end 60 of the catheter 50 that can withstand the environmental conditions of the body can be used in the catheter guidance system 2 of the present invention, in one particular embodiment, the external ultrasound transducer 48 can be in the form of any suitable transducer that can be disposed on or near the patient's body 78 having a small footprint such that it can be placed in a housing 49 configured to be placed on or near the patient's body 78. The external ultrasound transducer 48 may be any suitable transducer now known or later developed in the art. For example, in one embodiment, the external transducer 48 may be a piezoelectric (PZT) transducer. Alternatively, the external transducer 48 may be a capacitive micromachined ultrasonic transducer (CMUT). In yet another embodiment, the external transducer 48 may also include polydimethylsiloxane (PDMS) transducers and/or photoacoustic transducers. The manner in which the external ultrasound transducer 48 and the internal ultrasound transducer 46 function to identify the location of the catheter 50 is described in more detail below and with reference to Table 1.

TABLE 1

Attenuation v. Material at 1 MHz

| Material | $\alpha\left(\dfrac{dB}{MHz \cdot cm}\right)$ |
| --- | --- |
| Air, at 20° C. | 1.64 |
| Blood | 0.2 |
| Bone | 9.94 |
| Connective Tissue | 1.57 |
| Fat | 0.48 |
| Muscle | 1.09 |
| Soft Tissue (average) | 0.54 |
| Water | 0.0022 |

Ultrasound energy attenuates differently depending on the medium it travels through. For instance, as shown in Table 1 above, cartilage tissue has a higher attenuation factor ($\alpha$) compared to air and flesh. When the catheter 50 is located in the trachea 92, the catheter 50 will be surrounded by air, cartilage, and flesh. Notably, the cartilage forms 'rings' in the trachea 92. In comparison, when the catheter 50 is located in the esophagus 91, the catheter 50 will be surrounded by flesh and only a small amount of air, if any. Thus, ultrasound energy will be attenuated more within the trachea 92 due to the higher attenuation factor of cartilage than the attenuation of the same ultrasound energy within the esophagus 91.

Additionally, ultrasound energy is direction sensitive. Thus, the positioning of the external ultrasound transducer 48 relative to the ultrasound transducer 46 within the catheter 50 can impact the strength of the ultrasound energy detected by the external ultrasound transducer 48. For instance, the external ultrasound transducer 48 can be placed in a particular fixed location on the patient's body 78 or near the patient's body 78. For example, the external ultrasound transducer 48 may be placed on the side of the throat of the patient's body 78 in such a way that both the esophagus 91 and the trachea 92 are visible at the same time. The area in which the external ultrasound transducer 78 is capable of detecting ultrasound energy from within the patient is considered the "detection zone." The ultrasound transducer 46 within the catheter 50, e.g., at the tip 60 of the catheter 50, must pass through the detection zone in order for the external ultrasound transducer 48 to receive and detect the generated ultrasound energy from the ultrasound transducer 46 within the catheter 50.

In use, the ultrasound transducer 46 within the catheter 50 can be operated to generate ultrasound waves at a selected frequency and intensity such that the external ultrasound transducer 48, operating as a sensor or receiver of ultrasound energy, can detect the ultrasound energy generated by the transducer 46 when the catheter 50 is in the esophagus 91 but cannot detect the ultrasound energy generated by the transducer 46 when the catheter 50 is in the trachea 92. In other words, the selected frequency and intensity generated by the ultrasound transducer 46 within the catheter 50 is attenuated by the cartilage of the trachea 92 so that the ultrasound energy is not detectable when the ultrasound energy reaches the cartilaginous rings, while the ultrasound energy may be detectable when the catheter 50 is surrounded by air in the trachea 92 as it moves between cartilaginous rings. In some embodiments, the ultrasound waves can have a frequency ranging from about 20 kilohertz to about 2.5 megahertz, such as from about 25 kilohertz to about 2 megahertz, such as from about 50 kilohertz to about 1.5 megahertz. Further, in some embodiments, a spectrum or band of frequencies can be utilized rather than a single frequency within the aforementioned ranges.

Specifically, the external ultrasound transducer 48 functioning as a receiver may be able to "see" the catheter 50 when the catheter 50 is within the esophagus 91, and/or when the ultrasound transducer 46 of the catheter 50 is in between the cartilaginous rings of the trachea 92 (e.g., surrounded by air), but cannot "see" the catheter 50 when the ultrasound transducer 46 is behind or attenuated by the cartilaginous rings of the trachea 92. The external ultrasound transducer 48 can then send signals to the processor 20 relaying the received ultrasound information. The processor 20, and specifically one or more algorithms 23 stored in the memory device 21 in operative communication with the processor 20, can determine if the ultrasound signal generated by the ultrasound transducer 46 within the catheter 50 have been attenuated. For instance, attenuation can be determined as a "yes/no" or "pass/fail" determination. Additionally or alternatively, the amount or degree of attenuation can be measured, as a relative percentage of intensity or as an absolute value. The attenuation can be displayed by the display 22 in order to provide a visual indication of the location of the catheter 50.

In some embodiments, the ultrasound transducer 46 may additionally transmit a reference signal. The reference signal may be transmitted ultrasound energy having a selected frequency and intensity that is detectable when the catheter 50 is within both the esophagus 91 and the trachea 92. Thus, the reference signal can be used as confirmation that the catheter 50 is passing through the detection zone where the external ultrasound transducer 48 is configured to receive the ultrasound energy from the ultrasound transducer 46 within the catheter 50.

In some aspects of the invention, the function of the ultrasound transducer 46 within the catheter 50 and the external ultrasound transducer 48 can be reversed compared to the above-described procedure. The external ultrasound transducer 48 may generate ultrasound energy from its fixed location. The ultrasound transducer 46 within the catheter 50 may then be configured to receive the ultrasound energy generated by the external ultrasound transducer 48 to determine or measure the attenuation of the generated ultrasound energy. As described above, the ultrasound energy generated by the external ultrasound transducer 48 may be selected to have a frequency and intensity such that the attenuation by the cartilaginous tissue of the trachea 92 makes the ultrasound energy undetectable from the trachea 92 but still remains detectable from the esophagus 91. The ultrasound transducer 46 can then send signals to the processor 20 relaying the received ultrasound information. The processor 20, and specifically one or more algorithms 23 stored in the memory device 21 in operative communication with the processor 20, can determine if the ultrasound signal generated by the external ultrasound transducer 48 have been attenuated. For instance, attenuation can be determined as a "yes/no" or "pass/fail" determination. Additionally or alternatively, the amount or degree of attenuation can be measured, as a relative percentage of intensity or as an absolute value. The attenuation can be displayed by the display 22 in order to provide a visual indication of the location of the catheter 50.

In an additional arrangement for using ultrasound to detect the placement of the catheter 50, one or both of the ultrasound transducer 46 within the catheter 50 and the external ultrasound transducer 48 can be used to generate an ultrasound image that can be used to identify the location of the catheter 50. For instance, the ultrasound transducer 46 within the catheter 50 can be used alone (i.e., without being paired with the external ultrasound receiver 48) to generate ultrasound waves and receive reflected ultrasound waves to visualize or image the location of the catheter 50. Any suitable method of using ultrasound energy for visualizing tissue, e.g., ultrasound pulsing and measuring the reflected or echoed ultrasound waves, may be used. The reflected ultrasound waves within the trachea 92 have a distinctly different profile resulting in a different visual image compared to reflected ultrasound waves within the esophagus 91 to enable the user to distinguish between the presence of the catheter 50 in the trachea 92 or esophagus 91. Specifically, within the esophagus, which is a closed, tissue-dense environment, active ultrasound imaging may generate a glowing image showing the esophageal tissue, whereas the air-filled trachea 92 may show a dark image due to the air-filled environment. The ultrasound image may be shown on the display 22.

Additionally or alternatively, the memory device 21 may store one or more algorithms 23 such as machine-learning algorithms that are configured to differentiate between the visual images of esophageal tissue versus tracheal tissue and instruct the processor 20 what type of tissue in which the catheter 50 is located. For instance, machine learning algorithms may include mathematical models that are used to use input signals (e.g., data collected from the ultrasound transducer) to produce predictions (e.g., information regarding the position of the catheter). The parameters of these models can be selected based on training data that is collected in advance. Training data used for determining model parameters can be furnished from a-priori measurements from a selection of test subjects or models. Training data may also be collected on a subject-by-subject basis prior to beginning the placement of catheter. Finally, model parameters may be updated in real-time based on data that is collected during the procedure. Some examples of machine learning algorithms and mathematical models include, but are not limited to, decision trees, artificial neural networks, support vector machines, regression analyses, Bayesian networks, genetic algorithms, and deep learning algorithms.

Additionally or alternatively, an ultrasound time-of-flight calculation can be used to determine the location of the catheter 50. This can be performed either by the ultrasound transducer 46 of the catheter 50 on its own, by calculating the time-of-flight of waves generated and reflected back to the ultrasound transducer 46, or by measuring the time-of-flight of ultrasound waves generated by one of the ultrasound transducer 46 or the external ultrasound transducer 48 and received by the other respective ultrasound transducer. For instance, the processor 20 can send at least one time-stamped signal, e.g., at least one or a series of signals in the form of alternating current (AC), at a known frequency to the ultrasound transducer 46. By "time-stamped," the present invention contemplates recording the precise time that each respective signal is sent from the processor 20 to the ultrasound transducer 46. In this manner, it will be known at what time ultrasound transducer 46 within the catheter 50 generates an ultrasound signal at the known frequency. The external ultrasound transducer 48 receives the ultrasound signal that was generated from the ultrasound transducer 46 of the catheter 50 and measures the time that the signal was received. The external ultrasound transducer 48 then sends a signal back to the processor 20 containing information regarding the time the ultrasound signal was received. Thus, the processor 20, executing algorithms stored in the memory device 21, processes the signal received from the external ultrasound transducer 48 to calculate the "time-of-flight" of the ultrasound generated by the ultrasound transducer 46. Stated another way, using the known time stamp of the ultrasound signal generated by the ultrasound transducer 46 within the catheter 50 and the time stamp that the external ultrasound transducer 48 received the ultrasound signal that was generated by the ultrasound transducer 46, the processor 20 can determine the transit time of the ultrasound signal between the ultrasound transducer 46 of the catheter 50 and the external ultrasound transducer 48. Using the "time-of-flight" of the ultrasound signal generated by the ultrasound transducer 46, along with the estimated known distance from the external ultrasound transducer 48 to the trachea 92 and/or esophagus 91, the processor 20 then mathematically calculates a comparison between the time-of-flight or transit time to an estimated distance between the ultrasound transducer 46 of the catheter 50 and the external ultrasound transducer 48.

Further, in one embodiment and referring to FIG. 4, the catheter body 160 can have a plurality of markings 112 uniformly spaced along its external surface that can be used in conjunction with the ultrasound transducer 46 and external ultrasound transducer 48 to determine accurate placement of the catheter 50. These markings 112 can function as placement markers which assist the user in assessing the depth that the catheter 50 is placed within the body 78. For instance, when the ultrasound transducer 46 is located at the distal end 60 of the catheter 50, the markings 112 can be present from the distal end 60 of the catheter 50 to a point 126 on the catheter 50 that spans a distance that can correspond with the average distance between the trachea 92 and nostril 87 in a typical patient. As the catheter 50 is being inserted into the body 78 via the nostril 87, once the markings 112 are no longer visible outside the body 78, the user can instruct the system 2 to initiate the ultrasound transducer 46 and/or external ultrasound transducer 48 and start monitoring the display device 22 to observe the ultrasound signal attenuation, ultrasound image, or other calculations derived from the ultrasound signals as described above or to start monitoring for a visual indication, auditory indication, or both that the catheter 50 has be inserted into the correct (e.g., digestive tract) or incorrect location (e.g., respiratory tract). In an alternative embodiment, these markings 112 can assist the user in measuring the flow or distribution of liquid to or from the patient.

Further, as an alternative or in addition to generating and/or detecting ultrasound signals via the ultrasound transducer 46 and/or the external ultrasound transducer 48, the health care provider can also verify accurate placement of the catheter 50 in the esophagus 91 rather than the trachea 92 by observing for the presence or absence of a plurality of markings 112 uniformly spaced along the external surface of the catheter 50. As described above, such markings 112 can be used in conjunction with the ultrasound transducer 46 and external ultrasound transducer 48 to determine accurate placement of the catheter 50. These markings 112 can function as placement markers which assist the user in assessing the depth that the catheter 50 is placed within the body 78. For instance, when the ultrasound transducer 46 is located at the distal end 60 of the catheter 50, the markings 112 can be present from the distal end 60 of the catheter 50 to a point 126 on the catheter 50 that spans a distance that can correspond with the average distance between the trachea 92 and nostril 87 in a typical patient. As the catheter 50 is being inserted into the body 78 via the nostril 87, once the markings 112 are no longer visible outside the body 78, the health care provider can be alerted to start monitoring the display device 22 to observe the received ultrasound signal data and/or to start monitoring for a visual indication, auditory indication, or both that the catheter 50 has be inserted into the correct (e.g., digestive tract) or incorrect location (e.g., respiratory tract).

It should also be understood that multiple ultrasound transducers 46 and/or external ultrasound transducers 48 can be positioned at different spatial locations (i.e., multiple ultrasound transducers 46 placed along the length or around the circumference of the catheter 50; multiple external ultrasound transducers 48 placed in a special distribution on the skin externally, etc.). Also contemplated is the possibility of utilizing different frequencies or frequency ranges for each of the multiple ultrasound transducers 46 or each of the external ultrasound transducers 48, depending on which of the multiple ultrasound transducers (on the catheter or external) are transmitting the ultrasound waves. Specifically, when it comes to machine learning and pattern recognition, if the fidelity and certainty of data from one ultrasound transducer is not adequate, the machine learning algorithm's performance can be improved via the use of additional ultrasound transducers 46 and/or 48.

For instance, such an arrangement can be useful, for instance, when the ultrasound transducers 46 are placed around the circumference of the catheter 50, because at any given moment, one portion of the outer wall of the catheter 50 might stick to one wall of the esophagus 91 or trachea 92, while other portions of the outer wall of the catheter 50 may be resting in air (i.e., if you are in trachea). In fact, the mere presence of ultrasound transmission via ultrasound transducers 46 placed around the circumference of the catheter 50 may be enough to allow for differentiation between the trachea and the esophagus. For instance, by utilizing multiple ultrasound transducers 46 spaced around the outer wall of the catheter, the processor could be able to differentiate between the presence of the catheter 50 in the esophagus 91 or the trachea 92. This is because the outer wall of the catheter 50 would be exposed to air at least at some portions of its outer wall and to cartilage at some other portions of its outer wall in the trachea, which would result in different ultrasound frequency responses. Meanwhile, in the esophagus, the ultrasound transducers 46 would most likely only be exposed to muscle and tissue in the esophagus, where the frequency response would generally not change.

Regardless of the particular method by which proper placement of the catheter 50 is determined, once the distal end or tip 60 of the catheter 50 has been accurately placed within the desired location in the digestive tract, the health care provider can then optionally remove the ultrasound transducer 46 and/or external ultrasound transducer 48, particularly when the ultrasound transducer 46 is located within the lumen 70 of the catheter and includes a wired connection, where the wire assembly 62 electrically connects the ultrasound transducer 46 to the processor 20 via the electrical connector or controller coupler 36, while the position of the catheter 50 is maintained. The health care provider can then attach medicine and nutritional delivery tubes to the y-port connector 44 for introducing fluids into the body (e.g., digestive tract) for medical treatment. On the other hand, if the ultrasound transducer 46 is wireless, the ultrasound transducer 46 and external ultrasound transducer 48 can optionally be left in place, and the health care provider can then attach medicine and nutritional delivery tubes to the y-port connector 44 for introducing fluids into the body (e.g., digestive tract) for medical treatment.

Moreover, in conjunction with the ultrasound transducer 46 and external ultrasound transducer 48 described herein, the system 2 also contemplates the use of an optional signal generator 58 and associated transceiver 32 that can be used to track the position of the distal end 60 of the catheter 50 as it is being inserted into the patient's body 78. In one embodiment, the signal generator 58, which is located at the distal end 60 of the catheter and can be connected to the apparatus 10 via the controller coupler/electrical connected 36 and the wire assembly 62 (see FIGS. 1, 3, and 4), can be formed through one or a plurality of spirals or coils of wires. Further, the apparatus 10 can be configured to transmit electrical current through the wires such that the current travels in a circular path defined by the coils. This circular motion of current produces an electromagnetic field. In operation, when the apparatus 10 sends electrical current to the coils of the signal generator 58, the coils then transmit a signal or electromagnetic field capable of being detected by the non-invasive transceiver 32. The transceiver 32 then detects the electromagnetic field or signal generated by the signal generator 58 inside the patient's body 78 and the system 2 analyzes the resulting information to cause the display device 22 and the printer 28 to produce additional graphics 37 which can assist the health care provider in a catheter placement procedure in conjunction with ultrasound data acquired by the ultrasound transducer 46 and/or external ultrasound transducer 48. For instance, the system 2 can include a memory device 21 including machine readable instructions and one or more computer programs (which, for example, may include a plurality of algorithms 23) which are used by the processor 20 to process the signal data produced by the signal generator and transmitted by the transceiver 32, after which the processed data is displayed in graphical format on the display device 22 corresponding to the location of the distal end 60 of the catheter 50 within the patient's body 78. In one particular embodiment, the transceiver 32 can be used to determine the distance the signal generator 58 is from the transceiver 32 and its depth in the patient's body 78 can communicate with the display device 22 via the processor 20 to show a reference image of a non-subject body and an image of the signal generator 58 located on the display device 22 with the reference image.

Figure 6A:
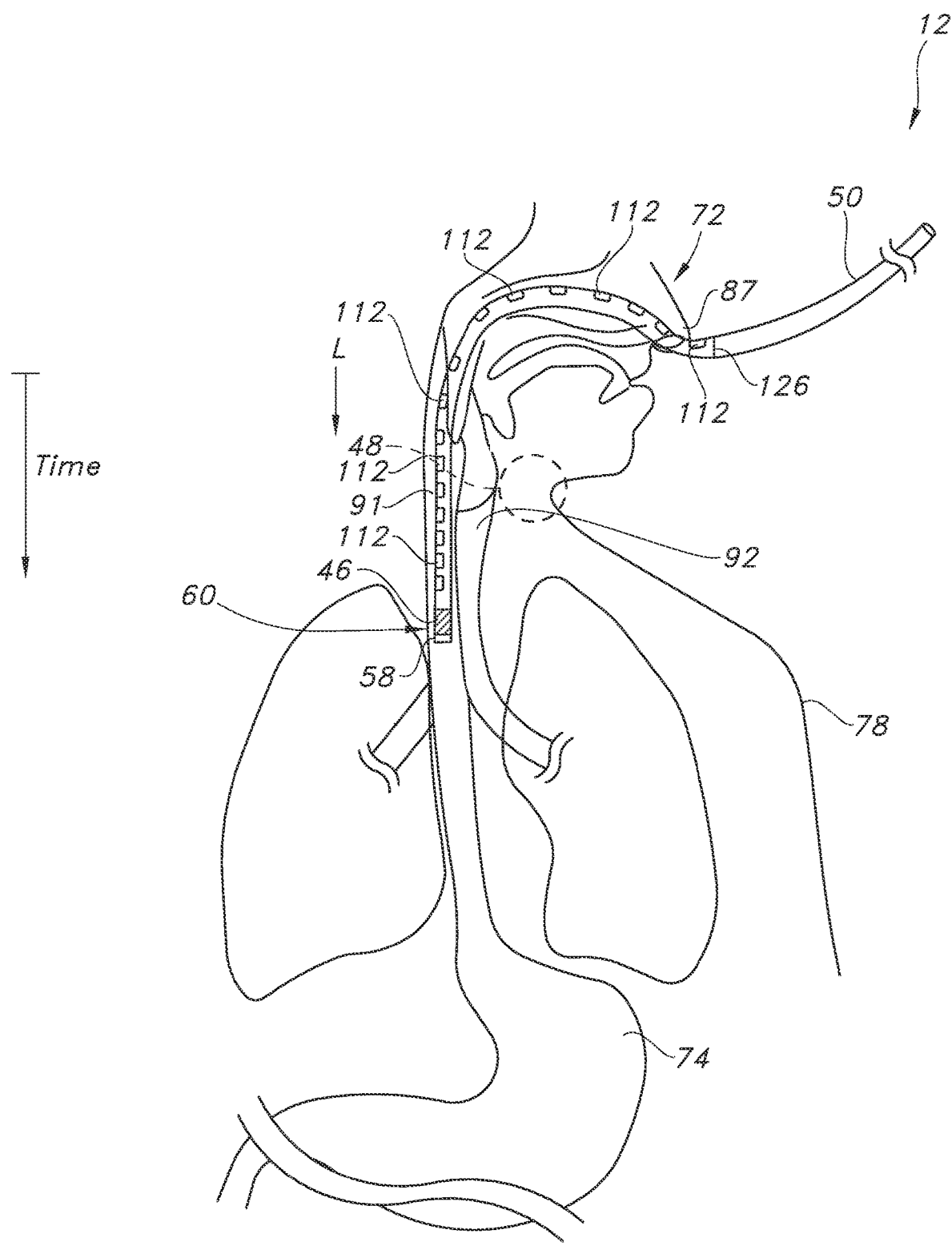
FIG. 6A is a top or plan view of a portion of the electronic catheter unit illustrating an enteral application involving insertion of a catheter into the esophagus of a patient, where the anatomical location of the catheter within the body can be monitored via ultrasound data generated by an ultrasound transducer and captured by the ultrasound transducer(s) of the present invention.
Figure 7A:
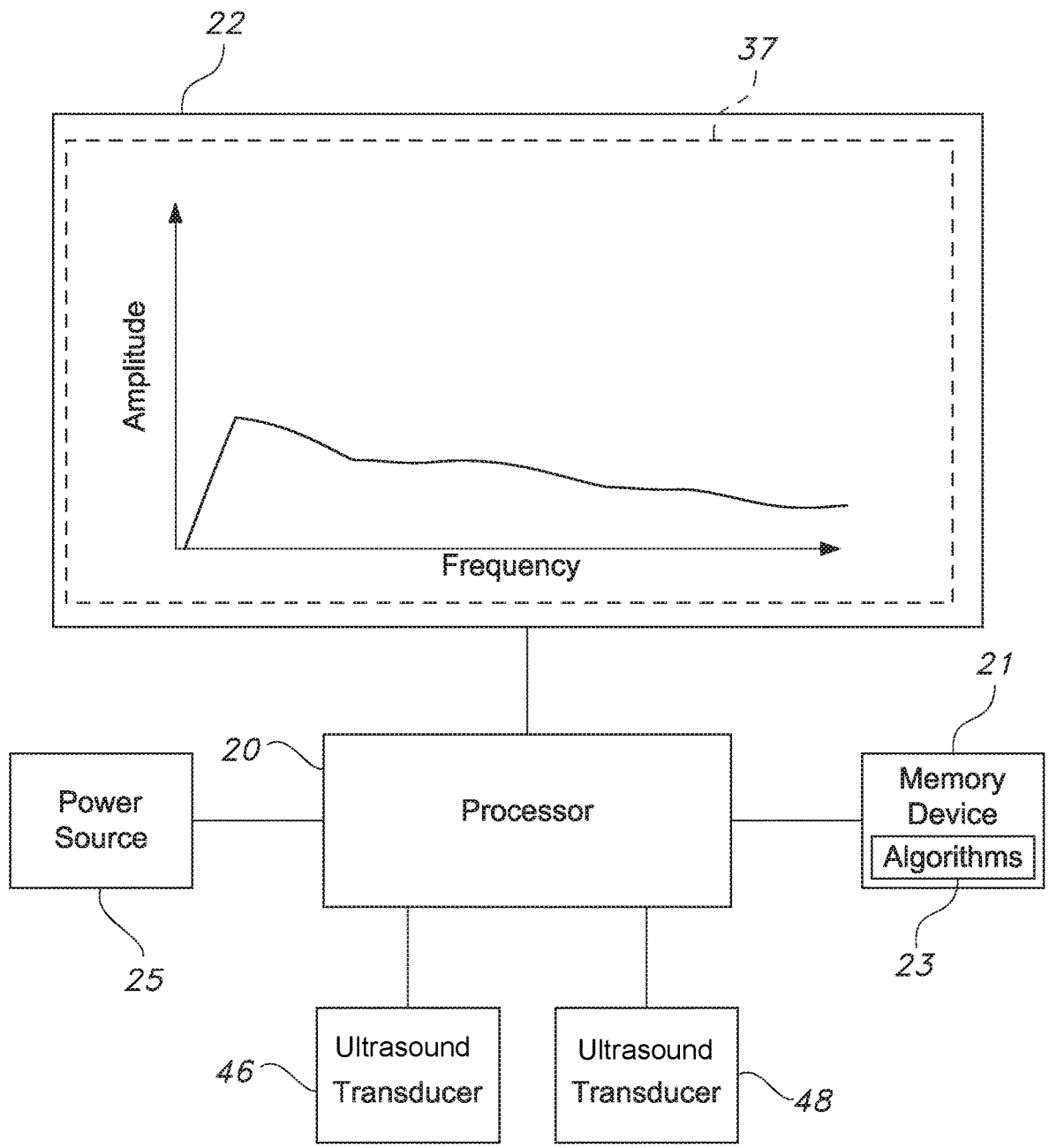
FIG. 7A is a schematic view of the catheter guidance system of the present invention as the system captures ultrasound data as the catheter of FIG. 6A is inserted into the esophagus and other anatomical regions of the digestive tract in real-time via the ultrasound transducers of the present invention.

FIG. 7A is a schematic view of the catheter guidance system 2 of the present invention as the system captures ultrasound data as the catheter 50 of FIG. 6A is inserted into the esophagus 91 and other anatomical regions of the digestive tract in real-time via the ultrasound transducers 46 and 48 of the present invention. The processor 20, memory device 21, and algorithms 23 can be used to analyze the data received from the ultrasound transducers 46 and 48 to cause a graph 37 to be shown on the display device 22, where the frequency and amplitude response are indicative of placement of the catheter 50 in the esophagus 91. Specifically, the frequency vs. amplitude graph 37 shows a sharp increase in amplitude then a gradual attenuation in amplitude as the frequency increases. This type of frequency response with a trend of a gradually decreasing amplitude is indicative of the behavior of the ultrasound waves as the waves travel through muscle and tissue in the esophagus 91.

Figure 6B:
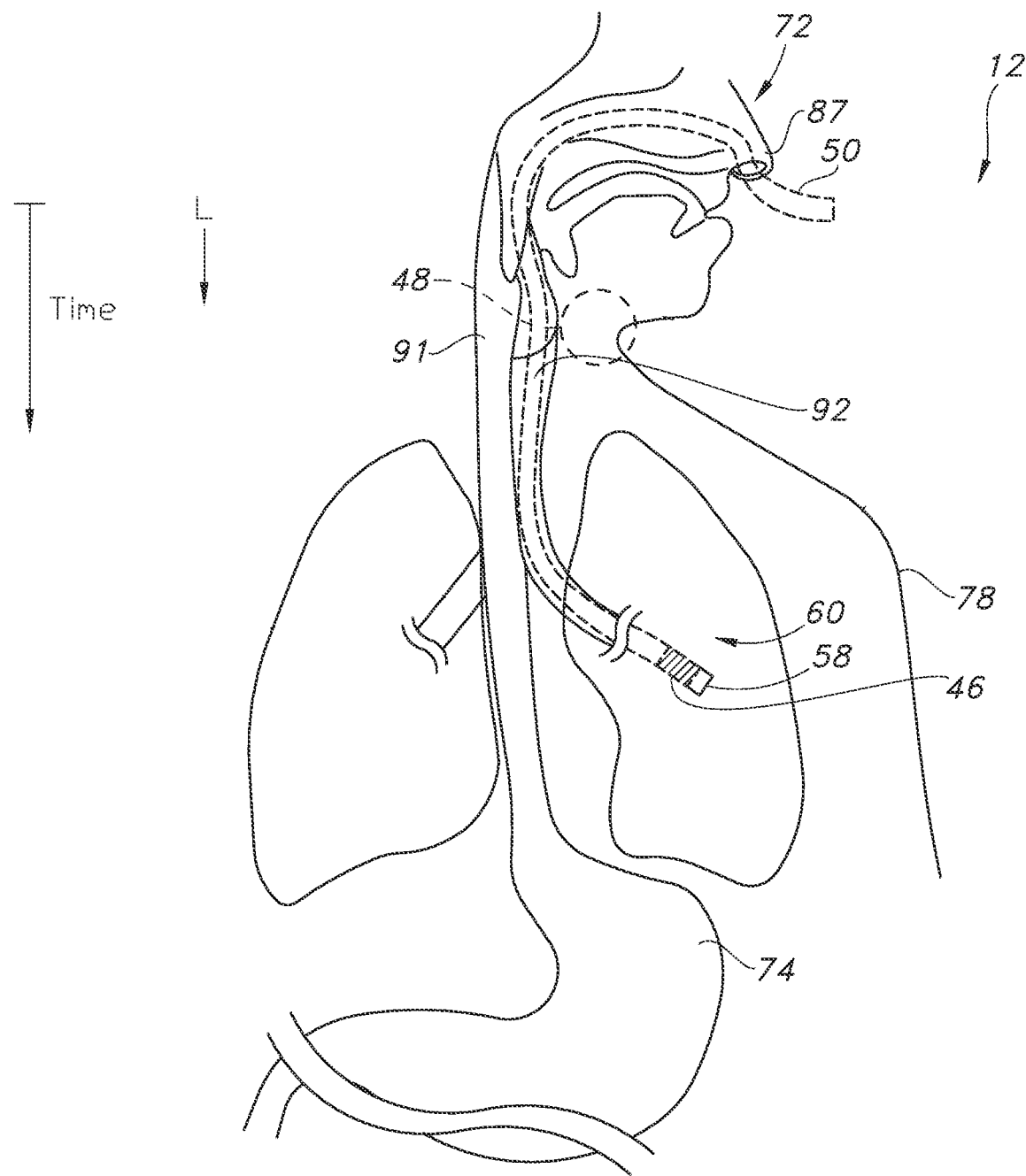
FIG. 6B is a top or plan view of a portion of the electronic catheter unit illustrating an enteral application involving insertion of a catheter into the lung of a patient, where the anatomical location of the catheter within the body can be monitored via ultrasound data generated by an ultrasound transducer and captured by the ultrasound transducer(s) of the present invention.
Figure 7B:
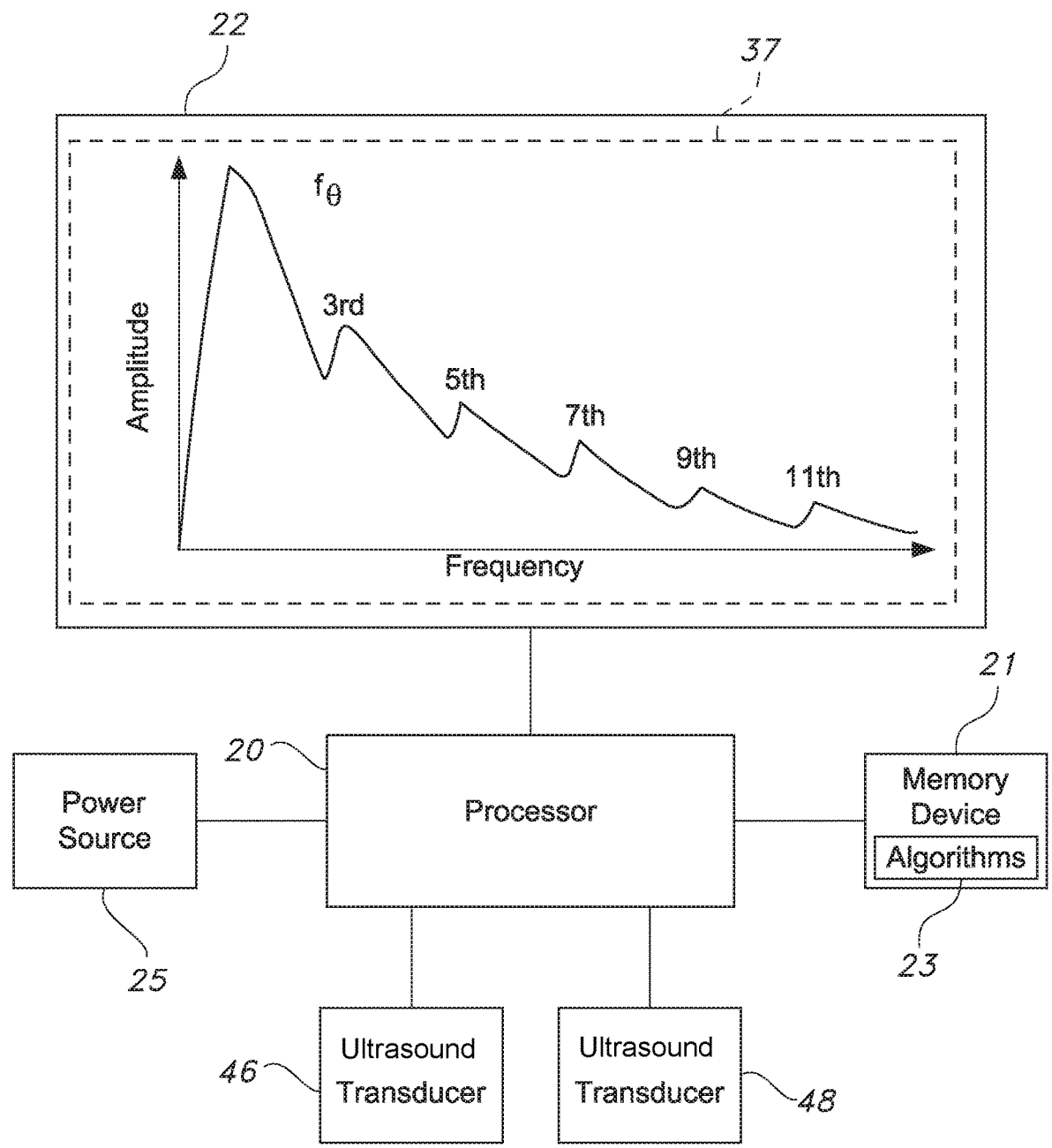
FIG. 7B is a schematic view of the catheter guidance system of the present invention as the system captures ultrasound data as the catheter of FIG. 6B is inserted into the trachea and other anatomical regions of the respiratory tract in real-time via the ultrasound transducers of the present invention.

FIG. 7B is a schematic view of the catheter guidance system 2 of the present invention as the system captures ultrasound data as the catheter 50 of FIG. 6B is inserted into the trachea 92 and other anatomical regions of the respiratory tract in real-time via the ultrasound transducers 46 and 48 of the present invention. The processor 20, memory device 21, and algorithms 23 can be used to analyze the data received from the ultrasound transducers 46 and 48 to cause a graph 37 to be shown on the display device 22, where the frequency and amplitude response are indicative of placement of the catheter 50 in the trachea 92. Specifically, the frequency vs. amplitude graph 37 shows attenuation in amplitude from the harmonic frequency $f_\theta$ to the $3^{rd}$, $5^{th}$, $7^{th}$, $9^{th}$ and $11^{th}$ harmonic frequencies. This type of frequency response with a trend of a decreasing amplitude but with sharp spikes of increased frequencies at the harmonic frequencies is indicative of the behavior of the ultrasound waves as the waves travel through air between rings of the cartilaginous tissue of the trachea 92.

It should also be appreciated that the tubing assembly, electronic catheter unit and catheter position guidance system of the present invention can be used in a variety of catheter procedures and applications. These procedures may involve the treatment of the digestive or gastrointestinal tract or other portions of the human body. Additionally, these procedures may involve the treatment of the respiratory tract of the human body, such as confirmation of tube location in an endotracheal tube insertion procedure. These procedures may involve treatment of humans by physicians, physician assistants, nurses or other health care providers. In addition, these procedures may involve treatment of other mammals and animals by veterinarians, researchers and others.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

This written description uses examples to disclose the invention, including the best mode, and also to enable any person skilled in the art to practice the invention, including making and using any devices or systems and performing any incorporated methods. The patentable scope of the invention is defined by the claims and may include other examples that occur to those skilled in the art. Such other examples are intended to be within the scope of the claims if they include structural elements that do not differ from the literal language of the claims or if they include equivalent structural elements with insubstantial differences from the literal language of the claims.

What is claimed is:

1. A catheter guidance system comprising:
   (A) a processor;
   (B) a power source;
   (C) a tubing assembly comprising:
      a catheter having a proximal end and a distal end and extending in a longitudinal direction, wherein the proximal end and the distal end define a lumen; and
      a plurality of ultrasound transducers placed approximately at the distal end of the catheter around the circumference and spaced around the outer wall of the catheter, wherein the plurality of ultrasound transducers transmit a continuous ultrasound energy or receive a continuous ultrasound energy transmitted from an external transducer as controlled by the processor in real-time via an electrical connection, wherein ultrasound data from the plurality of ultrasound transducers is communicated to the processor in real-time via an electrical connection;
   (D) a memory device storing instructions and algorithms which, when used by the processor, cause the processor to (i) interpret the ultrasound data communicated to the processor using the algorithms and (ii) cause the catheter guidance system to alert a user as to placement of the catheter in the digestive tract of the patient or alert the user as to placement of the catheter in the respiratory tract of the patient based on the interpretation of the ultrasound data;
   (E) the external ultrasound transducer, wherein the external ultrasound transducer is configured to transmit the continuous ultrasound energy to the plurality of ultrasound transducers of the tubing assembly or receive the continuous ultrasound energy transmitted by the plurality of ultrasound transducers of the tubing assembly,
   (F) a transceiver; and
   (G) a signal generator located at the distal end of the catheter that produces electronic signal data including a reference signal that is received by the transceiver, wherein the reference signal has a selected frequency and intensity that is detectable by the processor to confirm that the catheter is passing through a detection zone where the plurality of ultrasound transducers is configured to receive or transmit the continuous ultrasound energy, wherein the processor interprets the ultrasound data by determining a degree of attenuation of ultrasound signals, time-of-flight of ultrasound signals, or ultrasound images and interprets the electronic signal data received by the transceiver, wherein the degree of attenuation of the continuous ultrasound energy delivered at a frequency of about 20 kilohertz to about 2.5 megahertz is used to determine if the placement of the catheter is in the digestive tract or the respiratory tract, wherein the degree of attenuation is higher when the catheter is positioned in the respiratory tract than when the catheter is positioned in the digestive tract such that the continuous ultrasound energy transmitted by the plurality of ultrasound transducers is undetectable by the external ultrasound transducer when the plurality of ultrasound transducers is located within the respiratory tract or the continuous ultrasound energy transmitted by the external ultrasound transducer is undetectable by the plurality of ultrasound transducers when the plurality of ultrasound transducers is located within the respiratory tract.

2. The catheter guidance system of claim 1, wherein the plurality of ultrasound transducers comprise a piezoelectric component.

3. The catheter guidance system of claim 1, wherein the external ultrasound transducer is configured to be placed on or near the patient's throat or chest.

4. The catheter guidance system of claim 1, wherein more than one plurality of ultrasound transducers are placed along the length of the catheter around the circumference and spaced around the outer wall of the catheter.

5. The catheter guidance system of claim 1, wherein the continuous ultrasound energy by the external transducer or the plurality of ultrasound transducers is attenuated by cartilaginous rings of a trachea so that when the continuous ultrasound energy reaches the cartilaginous rings, the continuous ultrasound energy is undetectable.

6. The catheter guidance system of claim 1, wherein the electronic signals are an electromagnetic field or signal generated by the signal generator.

7. The catheter guidance system of claim 1, wherein the algorithms include at least one machine learning model or algorithm.

* * * * *